United States Patent [19]

Raddatz et al.

[11] Patent Number: 5,091,392

[45] Date of Patent: Feb. 25, 1992

[54] SUBSTITUTED (QUINOLIN-2-YL-METHOXY)PHENYL-ACYL-SULPHON-AMIDES AND -CYANAMIDES, PROCESSES FOR THEIR PREPARATION AND THEIR USE IN MEDICAMENTS

[75] Inventors: Siegfried Raddatz, Cologne; Klaus-Helmut Mohrs, Wuppertal; Romanis Fruchtmann, Cologne; Christian Kohlsdorfer, Erftstadt; Pia Theisen-Popp; Reiner Müller-Peddinghaus, both of Bergisch Gladbach, all of Fed. Rep. of Germany

[73] Assignee: Bayer Aktiengesellschaft, Leverkusen, Fed. Rep. of Germany

[21] Appl. No.: 517,108

[22] Filed: May 1, 1990

[30] Foreign Application Priority Data

May 23, 1989 [DE] Fed. Rep. of Germany ....... 3916663

[51] Int. Cl.$^5$ .................. A61K 31/47; C07D 215/00; C07D 215/12; C07D 215/16
[52] U.S. Cl. .................... 514/311; 546/152; 546/176; 546/153; 546/155; 546/156; 546/159; 546/160; 546/161; 546/170; 546/171; 546/172; 546/175; 514/312; 514/313
[58] Field of Search ............... 546/152, 176, 153, 155, 546/156, 159, 160, 162, 170, 171, 172, 175; 514/312, 313, 311

[56] References Cited

FOREIGN PATENT DOCUMENTS 219308 4/1987 European Pat. Off. ............ 546/176
2202223 9/1988 United Kingdom ............... 546/176

*Primary Examiner*—Mary C. Lee
*Assistant Examiner*—Robert C. Whittenbaugh
*Attorney, Agent, or Firm*—Sprung, Horn, Kramer & Woods

[57] ABSTRACT

A quinolin-2-yl-methoxy)phenylacyl-sulphonamide or -cyanamide of the formula

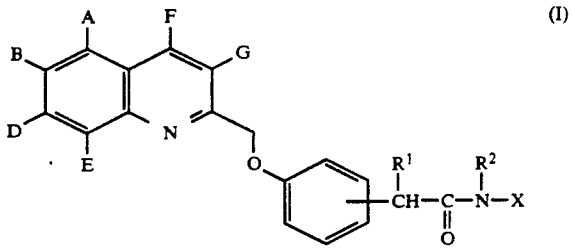

(I)

in which
A, B, D, E, F and G are identical or different and
represent hydrogen, hydroxyl, halogen, carboxyl, nitro, trifluoromethyl, trifluoromethoxy or a group of the formula $-NH^3R^4$, in which
$R^3$ and $R^4$ are identical or different and denote hydrogen, straight-chain or branched alkyl having up to 8 carbon atoms or aryl having 6 to 10 carbon atoms,
represent straight-chain or branched alkyl, alkoxy or alkoxycarbonyl in each case having up to 12 carbon atoms,
represent aryl having 6 to 10 carbon atoms,
$R^1$ represents cycloalkyl having 3 to 8 carbon atoms,
$R^2$ represents hydrogen or
straight-chain or branched alkyl having up to 10 carbon atoms,
represents an alkali metal,
represents cycloalkyl having 3 to 8 carbon atoms,
X represents a group of the formula $-SO_2-R^5$, in which
$R^5$ denotes trifluoromethyl or straight-chain or branches alkyl having up to 10 carbon atoms, or
denotes aryl having 6 to 10 carbon atoms, or
X represents cyano and physiologically acceptable salts thereof.

The (quinolin-2-yl-methoxy)phenylacylsulphonamide or -cyanamide is useful as an active compound in medicaments, particularly as a lipoxygenase inhibitor.

17 Claims, No Drawings

SUBSTITUTED (QUINOLIN-2-YL-METHOXY)PHENYL-ACYL-SULPHON-AMIDES AND -CYANAMIDES, PROCESSES FOR THEIR PREPARATION AND THEIR USE IN MEDICAMENTS

BACKGROUND OF THE INVENTION

1. Field of the Invention

The invention relates to new substituted (quinolin-2-yl-methoxy)phenylacyl-sulphonamides and -cyanamides, to processes for their preparation and to their use in medicaments.

2. Background Information

It is known that N-(phenylmethoxy)-3-(2-quinolin-2-yl-methoxy)benzeneacetamide derivatives have an antiallergic, antiasthmatic and antiinflammatory action [cf. U.S. Pat. No. 4,769,461]. In EP-A2 0,219,308, 2-substituted quinoline derivatives having antiasthmatic, antiallergic and antiinflammatory action are described whose substituent definition also includes the acylsulphonamido group.

SUMMARY OF THE INVENTION

Substituted (quinolin-2-yl-methoxy)phenylacyl-sulphonamides and -cyanamides of the general formula (I)

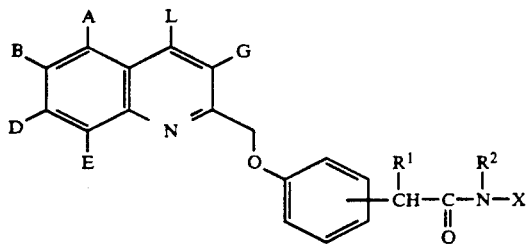

in which

A, B, D, E, L and G are identical or different and
represent hydrogen, hydroxyl, halogen, carboxyl, nitro, trifluoromethyl, trifluoromethoxy or a group of the formula $-NR^3R^4$, in which
$R^3$ and $R^4$ are identical or different and denote hydrogen, straight-chain or branched alkyl having up to 8 carbon atoms or aryl having 6 to 10 carbon atoms,
represent straight-chain or branched alkyl, alkoxy or alkoxycarbonyl in each case having up to 12 carbon atoms, and each of which is optionally substituted by hydroxyl, halogen, nitro, cyano or a group of the formula $-NR^3R^4$, in which $R^3$ and $R^4$ have the abovementioned meanings,
represent aryl having 6 to 10 carbon atoms, which is optionally substituted by halogen, hydroxyl, nitro, cyano, straight-chain or branched alkyl, alkoxy or alkoxycarbonyl in each case having up to 8 carbon atoms or by a group of the formula $-NR^3R^4$, in which $R^3$ and $R^4$ have the abovementioned meanings, $R^1$ represents cycloalkyl having 3 to 14 carbon atoms, which is optionally substituted by straight-chain or branched alkyl having up to 8 carbon atoms, $R^2$ represents hydrogen or
straight-chain or branched alkyl having up to 10 carbon atoms, which is optionally substituted by hydroxyl, alkoxy having up to 8 carbon atoms, halogen or by cycloalkyl having 3 to 8 carbon atoms or aryl having 6 to 10 carbon atoms, which in turn may be substituted by straight-chain or branched alkyl having up to 8 carbon atoms, halogen, nitro, hydroxyl or cyano, or
represents cycloalkyl having 3 to 8 carbon atoms which is optionally substituted by straight-chain or branched alkyl having up to 8 carbon atoms, or
represents an alkali metal, X represents a group of the formula $-SO_2-R^5$, in which
$R^5$ denotes trifluoromethyl or straight-chain or branched alkyl having up to 10 carbon atoms, which is optionally substituted by hydroxyl, halogen, cyano, alkoxy or alkoxycarbonyl in each case having up to 8 carbon atoms or by aryl having 6 to 10 carbon atoms, which in turn may be substituted by halogen, nitro, cyano or straight-chain or branched alkyl or alkoxy in each case having up to 8 carbon atoms, or
denotes aryl having 6 to 10 carbon atoms, which is optionally substituted by halogen, nitro, cyano, hydroxyl, straight-chain or branched alkyl, alkoxy or alkoxycarbonyl in each case having up to 8 carbon atoms, trifluoromethyl or trifluoromethoxy, or X represents cyano and their physiologically acceptable salts have now been found.

DETAILED DESCRIPTION OF THE INVENTION

In the context of the present invention, physiologically acceptable salts are preferred. Physiologically acceptable salts of the substituted (quinolin-2-yl-methoxy)phenylacyl-sulphonamides and -cyanamides may be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are also salts of the monovalent metals, such as alkali metals, and the ammonium salts. Sodium salts, potassium salts and ammonium salts are preferred.

The compounds according to the invention may exist in stereoisomeric forms which behave either as image and mirror image (enantiomers) or which do not behave as image and mirror image (diastereomers). The invention relates both to the antipodes and to the racemates, and also to the diastereomeric mixtures. The racemates, like the diastereomers, can be separated into the stereoisomerically homogeneous constituents in a known manner (cf. E. L. Eliel, Stereochemistry of Carbon Compounds, McGraw Hill, 1962).

Preferred compounds of the general formula (I) are those in which

A, B, D, E, L and G are identical or different and
represent hydrogen, hydroxyl, fluorine, chlorine, bromine, carboxyl, nitro, trifluoromethyl, trifluoromethoxy or a group of the formula $-NR^3R^4$, in which R³ and R⁴ are identical or different and denote hydrogen, straight-chain or branched alkyl having up to 6 carbon atoms or phenyl, represent straight-chain or branched alkyl, alkoxy or alkoxycarbonyl in each case having up to 10 carbon atoms, and each of which is optionally substituted by hydroxyl, fluorine, chlorine, bromine, nitro, cyano or a group of the formula —NR³R⁴, in which R³ and R⁴ have the abovementioned meanings, represent phenyl which is optionally substituted by fluorine, chlorine, bromine, hydroxyl, nitro, cyano, straight-chain or branched alkyl, alkoxy or alkoxycarbonyl in each case having up to 6 carbon atoms or by a group of the formula —NR³R⁴, in which R³ and R⁴ have the abovementioned meanings, R¹ represents cyclopropyl, cyclobutyl, cyclopentyl, cycloheptyl, cyclohexyl, cycloheptyl, cyclooctyl, cyclodecyl or cyclododecyl, each of which is optionally substituted by straight-chain or branched alkyl having up to 6 carbon atoms, R² represents hydrogen or
straight-chain or branched alkyl having up to 8 carbon atoms, which is optionally substituted by hydroxyl, alkoxy having up to 6 carbon atoms, fluorine, chlorine, bromine, cyclopropyl, cyclobutyl, cyclopentyl, cyclohexyl, cycloheptyl or phenyl, which in turn may be substituted by straight-chain or branched alkyl having up to 6 carbon atoms, fluorine, chlorine or bromine, or represents cyclopropyl, cyclohexyl, cyclopentyl, cyclohexyl or cycloheptyl, each of which is optionally substituted by straight-chain or branched alkyl having up to 6 carbon atoms, or represents sodium or potassium, X represents a group of the formula —SO₂—R⁵, in which R⁵ denotes trifluoromethyl or straight-chain or branched alkyl having up to 8 carbon atoms, which is optionally substituted by fluorine, chlorine, bromine, alkoxycarbonyl in each case having up to 6 carbon atoms or by phenyl, which in turn may be substituted by fluorine, chlorine, bromine or by straight-chain or branched alkyl or alkoxy in each case having up to 6 carbon atoms, or denotes phenyl which is optionally substituted by fluorine, chlorine, bromine, nitro, cyano, straight-chain or branched alkyl, alkoxy or alkoxycarbonyl in each case having up to 6 carbon atoms or trifluoromethyl, or X represents cyano and their physiologically acceptable salts.

Particularly preferred compounds of the general formula (I) are those in which

A, B, D, E, L and G are identical or different and represent hydrogen, fluorine, chlorine, bromine, nitro or trifluoromethyl, represent methyl, ethyl, propyl, isopropyl, butyl or tert.butyl, R¹ represents cyclopropyl, cyclobutyl, cyclopentyl, cyclohexyl, cyclooctyl, cyclodecyl or cyclododecyl, each of which is optionally substituted by methyl, ethyl, propyl or isopropyl, R² represents hydrogen or
straight-chain or branched alkyl having up to 6 carbon atoms, which is optionally substituted by cyclopropyl, cyclopentyl, cyclohexyl or cycloheptyl, represents cyclopropyl, cyclopentyl, cyclohexyl or cycloheptyl, or represents sodium, X represents a group of the formula —SO₂—R⁵, in which R⁵ denotes trifluoromethyl, straight-chain or branched alkyl having up to 6 carbon atoms, which is optionally substituted by phenyl which in turn is substituted by fluorine, chlorine or by straight-chain or branched alkyl having up to 4 carbon atoms, or denotes phenyl which may optionally be substituted by fluorine, chlorine or straight-chain or branched alkyl having up to 4 carbon atoms, or X represents cyano and their physiologically acceptable salts.

The compounds of the general formula (I) according to the invention

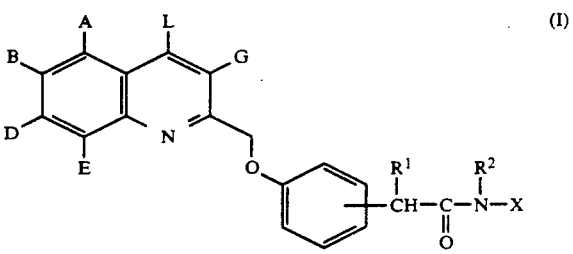

in which

A, B, D, E, L, G, R¹, R² and X have the abovementioned meanings, can be prepared by amidating carboxylic acids of the general formula (II)

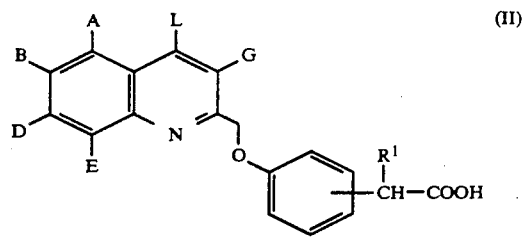

in which

A, B, D, E, L, G and R¹ have the abovementioned meanings, with amides of the general formula (III)

in which

R² and X have the abovementioned meanings, in inert solvents, if appropriate in the presence of dehydrating agents.

(Quinolin-2-yl-methoxy)phenylacyl-sulphonamides of the general formula (Ia)

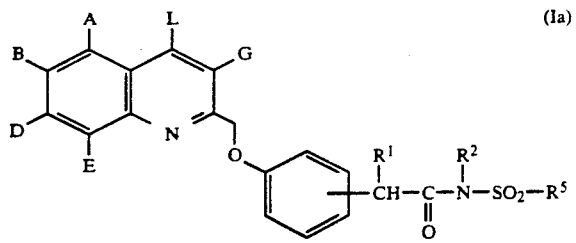

(Ia)

in which A, B, D, E, L, G, $R^1$, $R^2$ and $R^5$ have the above-mentioned meanings, can also be prepared by a process variant by first converting the carboxylic acids of the general formula (II) via the acid halide or anhydride stages according to customary methods to the corresponding acid amides of the general formula (IV)

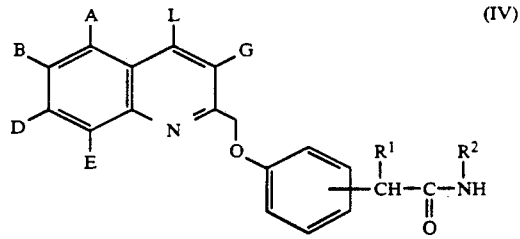

(IV)

in which
A, B, D, E, L, G, $R^1$ and $R^2$ have the abovementioned meanings,
and in a second step sulphonating with sulphonyl halides of the general formula (V)

$$X\text{—Hal} \qquad (V)$$

in which
X in this case represents the group $-SO_2-R^5$, in which $R^5$ has the abovementioned meaning, and
Hal represents fluorine, chlorine, bromine or iodine, in inert solvents.

The process according to the invention can be illustrated by way of example by means of the following equations:

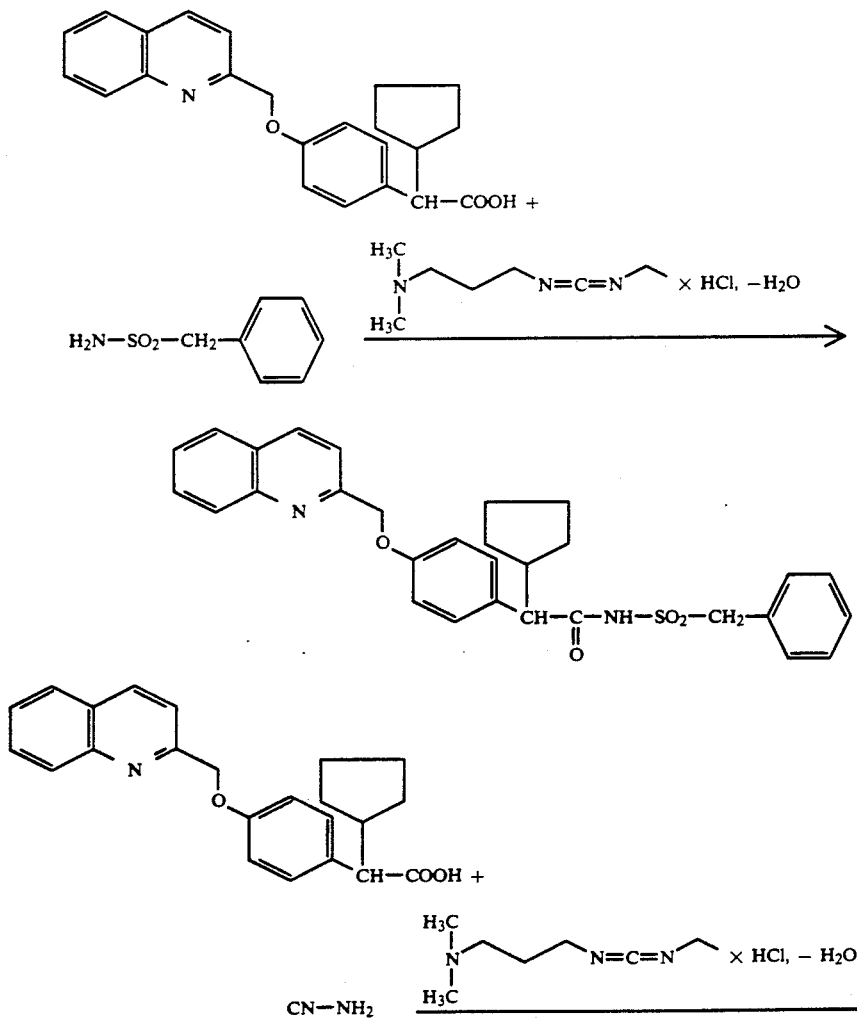

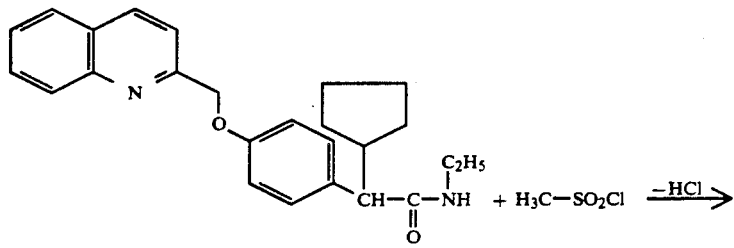

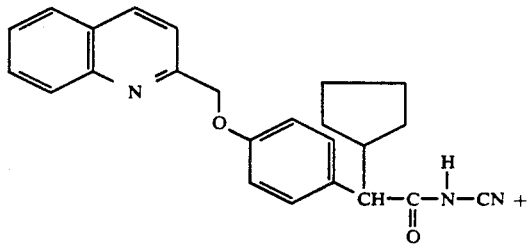

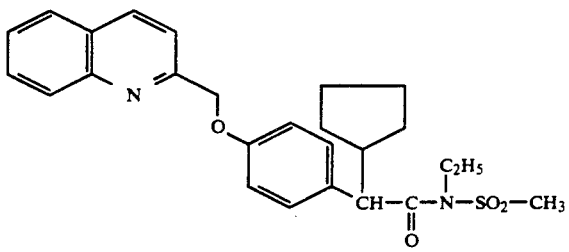

The amidation of the compounds of the general formula (II) is in general carried out in inert solvents in the presence of a base and a dehydrating agent.

Suitable solvents in this connection are inert organic solvents which do not change under the reaction conditions. These include halogenated hydrocarbons such as dichloromethane, trichloromethane, tetrachloromethane, 1,2-dichloroethane, trichloroethane, tetrachloromethane, 1,2-dichloroethane or trichloroethylene, hydrocarbons such as benzene, xylene, toluene, hexane, cyclohexane, or mineral oil fractions, nitromethane, dimethylformamide, acetonitrile or hexamethylphosphoramide. It is also possible to employ mixtures of the solvents. Dichloromethane is particularly preferred.

Suitable bases for the amidation are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate, potassium carbonate, or alkali metal alkoxides such as, for example, sodium methoxide or ethoxide, potassium methoxide or ethoxide or potassium tert.-butoxide, or organic amines such as benzyltrimethylammonium hydroxide, tetrabutylammonium hydroxide, pyridine, triethylamine or N-methylpiperidine.

The amidation is generally carried out in a temperature range from 0° C. to 150° C., preferably at 25° to 40° C.

The amidation is generally carried out at normal pressure. However, it is also possible to carry out the process at reduced pressure or at elevated pressure (for example in a range from 0.5 to 5 bar).

When carrying out the amidation, the base is generally employed in an amount from 1 to 3 moles, preferably from 1 to 1.5 moles, relative to 1 mole of the carboxylic acid of the general formula (II).

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphoric anhydride or isobutyl chloroformate or benzotriazolyloxy-tris-(dimethylamino)-phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. Ledis, J. Am. Chem. Soc. 95, 875 (1973); F. E. Frerman et al., J. Biol. Chem. 225, 2199, (1980) and N. B. Benoiton, K. Kuroda, Int. J. Pept. Prot. Res. 13, 403 (1979), 17, 187 (1981)].

The sulphonation of the compounds of the general formula (IV) is carried out in the abovementioned inert solvents, if appropriate using the bases and dehydrating agents also mentioned above.

The sulphonation is generally carried out at normal pressure. However, it is also possible to carry out the process at reduced pressure or elevated pressure (for example in a range from 0.5 to 5 bar).

The sulphonation is generally carried out in a temperature range from 0° C. to 150° C., preferably from +25° C. to +40° C.

The compounds of the general formula (III) are known or can be prepared by customary methods [cf. Houben-Weyl, "Methoden der organischen Chemie" (Methods of Organic Chemistry), volume IX, p. 407 ff and J. March, Advanced Organic Chemistry, Second Edition (1977) [cf. J. March, "Advanced Organic Chemistry", Second Edition p. 824 ff. (1977)].

The compounds of the general formulae (II) and (IV) are new and can be prepared, for example, by etherifying compounds of the general formulae (VI) or (VII)

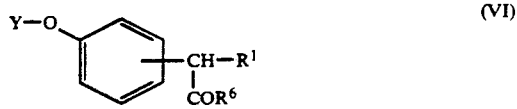

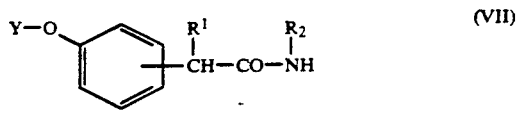

in which

R$^1$ and R$^2$ have the abovementioned meanings,

R$^6$ represents hydroxyl, C$_1$-C$_6$-alkoxy or phenyloxy, and

Y represents a typical hydroxyl protective group, such as, for example, benzyl or tert. butyl, after removal of the protective group by the customary method, with halomethylquinolines of the general formula (VIII)

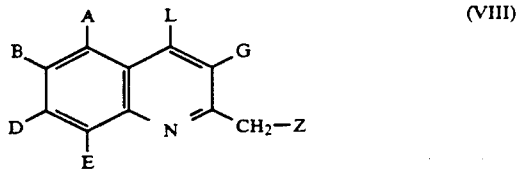

in which

A, B, D, E, L and G are identical or different and have the abovementioned meanings and Z represents halogen in inert solvents, if appropriate in the presence of a base or in the case of the compounds of the formula II in addition by alkylating compounds of the formula (IX)

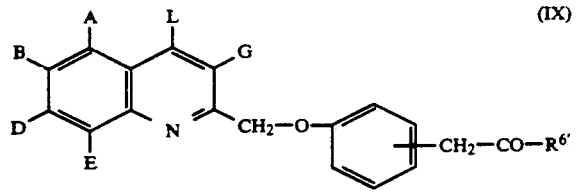

wherein

A, B, D, E, L and G have the abovementioned meanings and

R$^{6'}$ has the abovementioned meaning of R$^6$ but does not represent hydroxy, directly with compounds of the formula (X)

 (X)

wherein

R$^1$ has the abovementioned meaning and y represents halogen, preferably bromine, and in the case of the acids hydrolyzing the esters.

The removal of the protective groups from the corresponding ethers is carried out by the customary method, for example, by hydrogenolytic cleavage of the benzyl ethers in the abovementioned inert solvents with hydrogen gas in the presence of a catalyst [cf. also Th. Greene: "Protective Groups in Organic Synthesis", J. Wiley & Sons, 1981, New York].

The etherification can be carried out in inert organic solvents, if appropriate in the presence of a base.

Solvents for the etherification may be inert organic solvents which do not change under the reaction conditions. These preferably include ethers such as, for example, dioxane, tetrahydrofuran or diethyl ether, halogenated hydrocarbons such as dichloromethane, trichloromethane, tetrachloromethane, 1,2-dichloroethane or trichloroethylene, hydrocarbons such as benzene, xylene, toluene, hexane, cyclohexane or mineral oil fractions, nitromethane, dimethylformamide, acetonitrile, acetone or hexamethylphosphoramide. It is also possible to employ mixtures of the solvents.

Bases which can be employed for the etherification are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or organic amines (trialkyl(C$_1$-C$_6$)amines) such as triethylamine, or heterocycles such as pyridine, methylpiperidine, piperidine or morpholine.

It is also possible to employ alkali metals such as sodium, and their hydrides, such as sodium hydride, as bases.

The etherification is generally carried out in a temperature range from 0° C. to 150° C., preferably from 10° C. to 100° C. at normal pressure. However, it is also possible to carry out the etherification at reduced pressure or elevated pressure (for example in a range from 0.5 to 5 bar).

The hydrolysis of the carboxylic acid esters is carried out by customary methods by treating the esters in inert solvents with customary bases, it being possible to convert the salts initially formed into the free carboxylic acids by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogencarbonate or alkali metal alkoxides such as sodium ethoxide, sodium methoxide, potassium ethoxide, potassium methoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is generally carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is generally employed in an amount from 1 to 3 moles, preferably from 1 to 1.5 moles, relative to 1 mole of the ester. Molar amounts of the reactants are particularly preferably used.

When carrying out the reaction, the salts of the compounds according to the invention are formed in the first step as intermediates which can be isolated. The acids according to the invention are obtained by treating the salts with customary inorganic acids. These preferably include mineral acids such as, for example, hydrochloric acid, hydrobromic acid, sulphuric acid or phosphoric acid. In this connection, it has proved advantageous in the preparation of the carboxylic acids to acidify the basic reaction mixture from the hydrolysis in a second step without isolating the salts. The acids can then be isolated in a customary manner.

The alkylation of the C-H acid compounds (formula IX) with alkyl halides is in general carried out in inert solvents in the presence of a base.

Suitable solvents for this reaction are all the inert organic solvents, depending on the nature of the alkylating agent. These solvents include, preferably, ethers, such as diethyl ether, dioxane or tetrahydrofuran, or hydrocarbons, such as benzene, toluene or xylene, or dimethylformamide or hexamethylphosphoric acid triamide, or mixtures of the solvents mentioned.

Suitable bases are the customary basic compounds. These include, preferably, alkali metal hydrides, such as sodium hydride, alkali metal amides, such as sodium amide or lithium diisopropylamide, alkali metal alcoholates, such as sodium methanolate, sodium ethanolate, potassium methanolate, potassium ethanolate or potassium tert.-butylate, or organic amines, such as trialkylamines, for example triethylamine, or organolithium compounds, such as butyllithium or phenyllithium.

The alkylation of the CH-acid compounds is in general carried out in a temperature range from 0° C. to 150° C., preferably from 10° C. to 100° C.

The alkylation of the CH-acid compounds is in general carried out under normal pressure. However, it is also possible to carry out the process under reduced pressure or increased pressure (for example in a range from 0.5 to 5 bar).

In general, 0.5 to 5, preferably 1 to 2, mol of halide are employed per mol of the reaction partner. The base is in general employed in an amount of 0.5 to 5 mol, preferably 1 to 3 mol, based on the halide.

The compounds of the general formulae (VI) and (VII) are known per se or can be prepared by known methods [cf. H. Beyer, Lehrbuch der organischen Chemie (Textbook of Organic Chemistry), S. Hirzel Verlag, Stuttgart; Protective Groups in Organic Synthesis, J. Wiley & Sons, 1981, New York].

The halomethylquinolines of the general formula (VIII) are known or can be prepared by the customary method [cf. Chem. Ber., 120, 649, 1987].

The compounds of the general formula (X) are known. The compounds of the general formula (IX) are known or can be prepared by customary methods.

In order to prepare isomerically pure compounds of the general formula (I), the isomerically pure form of the starting compound can of course be employed directly. However, they can also be obtained by the customary methods of racemate separation.

The acylsulphonamides and acylcyanamides of the general formula (I) according to the invention can be employed as active compounds in medicaments. The compounds act particularly as inhibitors of enzymatic reactions in the context of arachidonic acid metabolism, in particular lipoxygenase.

They are thus suitable preferably for the treatment and prevention of disorders of the airways such as allergies/asthma, bronchitis, emphysema, shock lung, pulmonary hypertension, inflammations/rheumatism and oedemas, thromboses and thromboembolisms, ischaemias (peripheral, cardiac and cerebral circulatory disturbances), cardiac and cerebral infarcts, cardiac arrhythmias, angina pectoris, arteriosclerosis, in tissue transplants, dermatoses such as psoriasis, metastases and for cytoprotection in the gastrointestinal tract.

The pharmacological activity data of the substances according to the invention are determined by the following method:

As a measure of the lipoxygenase inhibition, the release of leucotriene $B_4$ ($LTB_4$) from polymorphonuclear rats leucocytes (PMNL) was determined after addition of substances and Ca ionophore by means of reverse phase HPLC according to Borgeat, P. et al., Proc. Nat. Acad. Sci., 76, 2148–2152 (1979). The in vivo activity of the compounds was detected using the mouse ear inflammation model according to Young, J. M. et al., J. of Investigative Dermatology, 82, 367–371 (1984).

In Table 1, the values obtained by this test for some compounds according to the invention are shown by way of example:

TABLE 1

| Example | LO inhibition $IC_{50}$ (mmol/l) |
|---|---|
| 1 | $2.7 \times 10^{-8}$ |
| 6 | $3.3 \times 10^{-8}$ |
| 7 | $2.4 \times 10^{-8}$ |

Using suitable inert non-toxic, pharmaceutical excipients or solvents, the new active compounds can be converted in a manner known per se into the customary formulations, such as tablets, capsules, coated tablets, pills, granules, aerosols, syrups, emulsions, suspensions and solutions. In this connection, the therapeutically active compound should in each case be present in the total mixture in a concentration of about 0.5 to 90% by weight, preferably from 10 to 70% by weight, i.e., in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, if appropriate organic solvents can be used as auxiliary solvents.

Examples of auxiliaries which may be mentioned are: water, non-toxic organic solvents such as paraffins (for example, mineral oil fractions), vegetable oils (for example, groundnut/sesame oil), alcohols (for example, ethyl alcohol, glycerol), glycols (for example, propylene glycol, polyethylene glycol), solid excipients, such as ground natural minerals (for example, kaolins, clays, talc, chalk), ground synthetic minerals (for example, highly disperse silica, silicates), sugars (for example, sucrose, lactose and dextrose), emulsifiers (for example, polyoxyethylene fatty acid esters, polyoxyethylene fatty alcohol ethers, alkylsulphonates and arylsulphonates), dispersants (for example, lignin-sulphite waste liquors, methyl cellulose, starch and polyvinylpyrrolidone) and lubricants (for example, magnesium stearate, talc, stearic acid and sodium lauryl sulphate).

Administration can be carried out in a customary manner, preferably orally or parenterally, in particular perlingually or intravenously. In the case of oral administration, tablets can of course also contain additions such as sodium citrate, calcium carbonate and dicalcium phosphate together with various additives, such as starch, preferably potato starch, gelatin and the like in addition to the excipients mentioned. Furthermore, lubricants such as magnesium stearate, sodium lauryl sulphate and talc can additionally be used for tableting. In the case of aqueous suspensions and/or elixirs, which are intended for oral administration, various flavor-improvers or colorants can be added to the active compounds in addition to the abovementioned auxiliaries.

For the case of parenteral administration, solutions of the active compounds can be employed using suitable liquid excipients.

In general, it has proved advantageous on intravenous administration to administer amounts of about 0.01 to 10 mg/kg, preferably about 0.01 to 5 mg/kg of body weight, to attain effective results. On oral administration, the dosage is in general about 0.1 to 200 mg/kg, preferably 1 to 100 mg/kg of body weight.

In spite of this it may be necessary to deviate from the amounts mentioned, depending on the body weight or type of application route, on individual behavior towards the medicament, the manner of its formulation and the point in time or interval at which administration takes place. Thus, in some cases it may be sufficient to manage with less than the minimum amount previously mentioned, while in other cases the upper limit mentioned must be exceeded. In the case of the administration of relatively large amounts, it may be advisable to divide these into a number of individual doses over the day.

The acylsulphonamides and acylcyanamides according to the invention can be used both in human medicine and in veterinary medicine.

PREPARATION EXAMPLES

EXAMPLE 1

N-{1-[4-(Quinolin-2-yl-methoxy)phenyl]-1-cyclopentyl}acetyl-methanesulphonamide

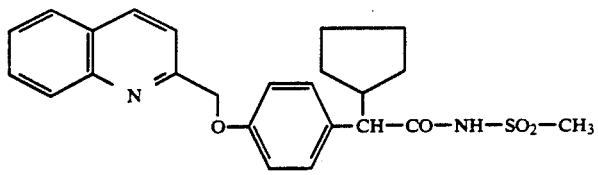

2.2 g (0.006 mol) of 1-[4-(quinolin-2-yl-methoxy)-phenyl]-1-cyclopentyl-acetic acid, 0.8 g (0.006 mol) of dimethylaminopyridine, 0.6 g (0.006 mol) of methanesulphonamide and 1.4 g (0.007 mol) of N-(3-dimethylaminopropyl)-N'-ethyl-carbodiimide hydrochloride are dissolved in 80 ml of dry dichloromethane and stirred at room temperature for 60 hours. The mixture is then concentrated to dryness in vacuo, the residue is suspended in 50 ml of dichloromethane and the mixture is extracted twice by shaking with 20 ml of water. The organic phase is dried, concentrated to a small volume and the mixture is separated by column chromatography (silica gel 60, eluent:dichloromethane/ethyl acetate/glacial acetic acid=100/5/1 to 100/10/1). Yield: 1.8 g (68.4% of theory) of a colorless amorphous product. M.p.: about 75° C.

EXAMPLE 2

N-{1-[4-(Quinolin-2-yl-methoxy)phenyl]-1-cyclopentyl}acetyl-benzylsulphonamide

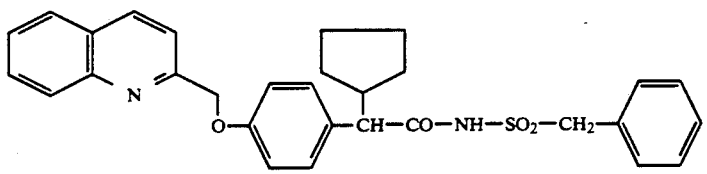

Analogously to the directions for Example 1, the title compound is prepared from 2.2 g (0.006 mol) of 1-[4-(quinolin-2-yl-methoxy)phenyl]-1-cyclopentyl-acetic acid, 0.8 g (0.006 mol) of dimethylaminopyridine, 1.1 g (0.006 mol) of benzylsulphonamide and 1.4 g (0.007 mol) of N-(3-dimethylaminopropyl)-N'-ethyl-carbodiimide hydrochloride. Yield: 1.9 g (61.5% of theory) of colorless crystals. M.p.: 171° C.

EXAMPLE 3

N-{1-[4-(Quinolin-2-yl-methoxy)phenyl]-1-cyclopentyl}acetyl-p-tolylsulphonamide

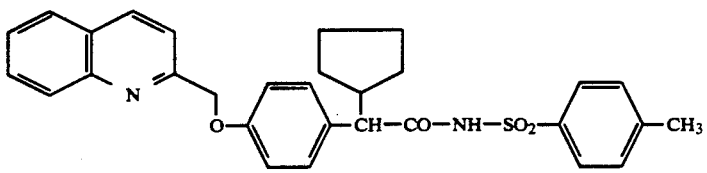

Analogously to the directions for Example 1, the title compound is prepared from 2.2 g (0.006 mol) of 1-[4-(quinolin-2-yl-methoxy)phenyl]-1-cyclopentyl-acetic acid, 0.8 g (0.006 mol) of dimethylaminopyridine, 1.1 g (0.006 mol) of p-tolylsulphonamide and 1.4 g (0.007 mol) of N-(3-dimethylaminopropyl)-N'-ethyl-carbodiimide hydrochloride. Yield: 2.3 g (74.5% of theory) of a colorless amorphous product. M.p.: about 80° C.

EXAMPLE 4

N-{1-[4-(Quinolin-2-yl-methoxy)phenyl]-1-cyclopentyl}-acetyl-o-tolylsulphonamide

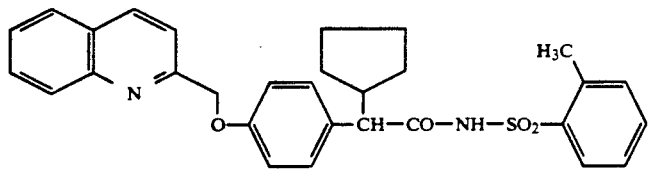

Analogously to the directions for Example 1, the title compound is prepared from 2.2 g (0.006 mol) of 1-[4-(quinolin-2-yl-methoxy)phenyl]-1-cyclopentyl-acetic acid, 0.8 g (0.006 mol) of dimethylaminopyridine, 1.1 g (0.006 mol) of o-tolylsulphonamide and 1.4 g (0.007 mol) of N-(3-dimethylaminopropyl)-N'-ethyl-carbodiimide hydrochloride. Yield: 2.2 g (71.3% of theory) of a colorless, amorphous product. M.p.: about 80° C.

EXAMPLE 5

N-{1-[4-(Quinolin-2-yl-methoxy)phenyl]-1-cyclopentyl}-acetyl-trifluoromethanesulphonamide

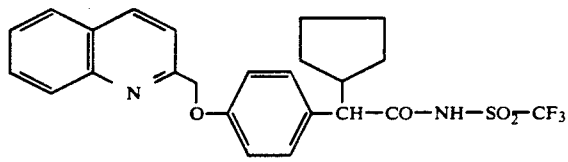

Analogously to the directions for Example 1, the title compound is prepared from 3.6 g (0.01 mol) of 1-[4-(quinolin-2-yl-methoxy)phenyl]-1-cyclopentyl-acetic acid, 1.3 g (0.01 mol) of dimethylaminopyridine, 1.9 g (0.01 mol) of trifluoromethanesulphonamide and 1.9 g (0.01 mol) of N-(3-dimethylaminopropyl)-N'-ethyl-carbodiimide hydrochloride. Yield: 3.7 g (75.1% of theory) of colorless crystals. M.p.: 252° C. (dec.).

EXAMPLE 6

N-Methyl-N-{1-[4-(quinolin-2-yl-methoxy)phenyl]-1-cyclopentyl-acetyl}-trifluoromethanesulphonamide

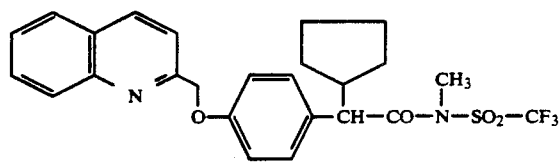

Analogously to the directions for Example 1, the title compound is prepared from 3.0 g (0.0083 mol) of 1-[4-(quinolin-2-yl-methoxy)phenyl]-1-cyclopentyl-acetic acid, 1.1 g (0.0083 mol) of dimethylaminopyridine, 1.4 g (0.0083 mol) of N-methyl-trifluoromethanesulphonamide and 1.6 g (0.0083 mol) of N-(3-dimethylaminopropyl)-N'-ethylcarbodiimide hydrochloride. Yield: 0.6 g (14.2% of theory) of a colorless oil.

EXAMPLE 7

N-{1-[4-(Quinolin-2-yl-methoxy)phenyl]-1-cyclopentyl}-acetyl-cyanamide

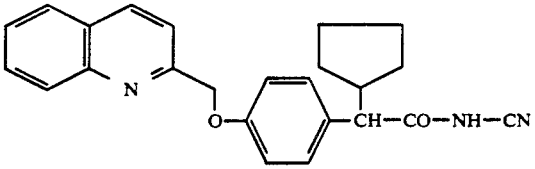

Analogously to the directions for Example 1, the title compound is prepared from 3.0 g (0.0083 mol) of 1-[4-(quinolin-2-yl-methoxy)phenyl]-1-cyclopentyl-acetic acid, 1.1 g (0.0083 mol) of dimethylaminopyridine, 0.42 g (0.0083 mol) of cyanamide and 1.6 g (0.0083 mol) of N-(3-dimethylaminopropyl)-N'-ethyl-carbodiimide hydrochloride. Yield: 1.9 g (59.4% of theory) of a colorless amorphous product. M.p.: about 90° C.

EXAMPLE 8

Sodium N-{1-[4-(quinolin-2-yl-methoxy)phenyl]-1-cyclopentyl}-acetyl-trifluoromethanesulphonamide

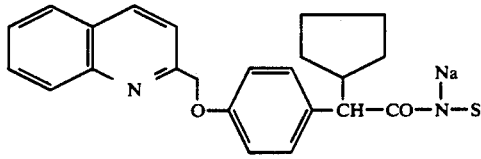

0.374 g (0.00076 mol) of the compound from Example 5 was dissolved in 20 ml of tetrahydrofuran/ethanol (1:1) and 0.76 ml (0.00076 mol) of 1 n sodium hydroxide solution was added dropwise to the solution. The solution was stirred for 15 minutes, completely evaporated to dryness in vacuo and dried in a desiccator. Yield: quantitative, colorless product. M.p.: 218° C. (dec.).

EXAMPLE 9

N-{1-[4-(quinolin-2-yl-methoxy)phenyl]-cyclohexyl}-acetylmethanesulphonamide

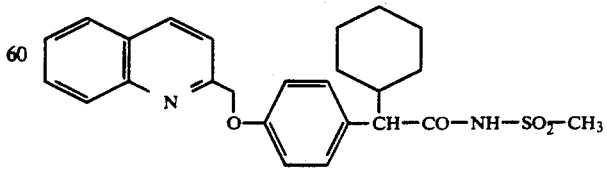

Analogously to the directions for Example 1 the title compound is prepared from 7 g (0.018 mol) of 1-[4-(quinolin-2-yl-methoxy)phenyl]-1-cyclohexyl-acetic acid, 2.3 g (0.018 mol) of dimethylaminopyridine, 1.8 g (0.018 mol) of methanesulphonamide and 4.8 g (0.025 mol) of N-(3-dimethylaminopropyl)-N'-ethyl-carbodiimide hydrochloride. Yield: 5.8 g (72% of theory) of a light yellow viscous oil.

EXAMPLE 10

N-{1-[4-(quinolin-2-yl-methoxy)phenyl]-cyclohexyl}-acetylbenzylsulphonamide

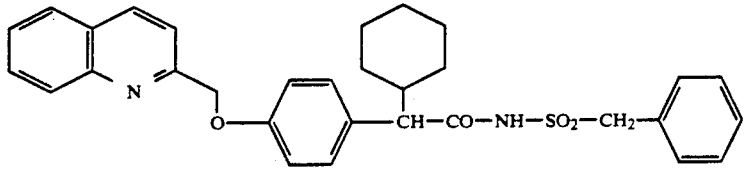

Analogously to the directions for Example 1 the title compound is prepared from 2.7 g (0.0072 mol) of 1-[4-(quinolin-2-yl-methoxy)phenyl]-1-cyclohexyl-acetic acid, 1.0 g (0.0078 mol) of dimethylaminopyridine, 1.3 g (0.0072 mol) of benzylsulphonamide and 1.5 g (0.0078 mol) of N-(3-dimethylaminopropyl)-N'-ethyl-carbodiimide hydrochloride. Yield: 2.8 g (74% of theory) of colourless crystals M.p. 123° C.

EXAMPLE 11

N-{1-[4-(quinolin-2-yl-methoxy)phenyl]-1-cyclohexyl}-acetyl-o-tolylsulphonamide

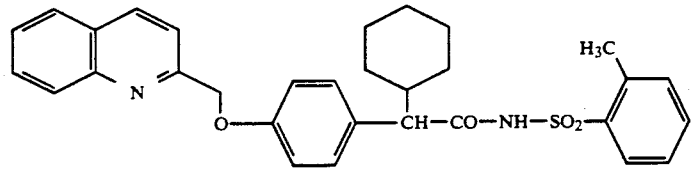

Analogously to the directions for Example 1 the title compound is prepared from 2 g (0.005 mol) of 1-[4-(quinolin-2-yl-methoxy)phenyl]-1-cyclohexyl-acetic acid, 0.6 g (0.005 mol) of dimethylaminopyridine, 0.9 g (0.005 mol) of o-tolylsulphonamide and 1.15 g (0.006 mol) of N-(3-dimethylaminopropyl)-N'-ethyl-carbodiimide hydrochloride. Yield: 2.5 g (94.6% of theory) of a light yellow, viscous oil.

EXAMPLE 12

N-{1-[4-(quinolin-2-yl-methoxy)phenyl]-1-cyclohexyl}-acetyl-cyanamide

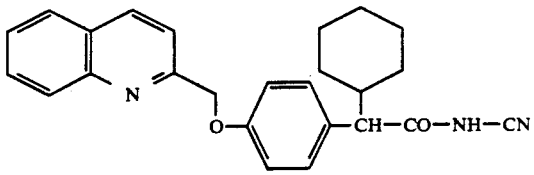

Analogously to the directions for Example 1 the title compound is prepared from 3.0 g (0.008 mol) of 1-[4-(quinolin-2-yl-methoxy)phenyl]-1-cyclohexyl-acetic acid, 1.0 g of dimethylaminopyridine, 0.4 g (0.008 mol) of cyanamide and 1.6 g (0.008 mol) of N-(3-dimethylaminopropyl)-N'-ethyl-carbodiimide hydrochloride. Yield: 2.0 g (62% of theory) of a colourless amorphous product. M.p.: about 90° C.

EXAMPLE 13

N-{1-[4-(quinolin-2-yl-methoxy)phenyl]-cycloheptyl}-acetyl-methanesulphonamide

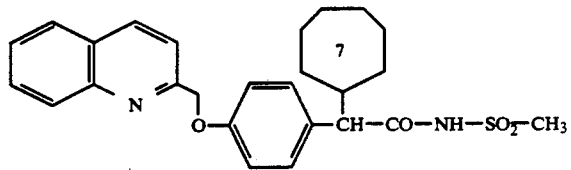

Analogously to the directions for Example 1 the title compound is prepared from 8 g (0.02 mol) of 1-[4-(quinolin-2-yl-methoxy)phenyl]-1-cycloheptyl-acetic acid, 2.4 g (0.02 mol) of dimethylaminopyridine, 1.9 g (0.02 mol) of methanesulphonamide and 5.7 g (0.03 mol) of N-(3-dimethylaminopropyl)-N'-ethyl-carbodiimide hydrochloride. Yield: 6.3 g (79% of theory) of colourless crystals. M.p.: 174°-6° C.

EXAMPLE 14

N-{1-[4-(quinolin-2-yl-methoxy)phenyl]-1-cycloheptyl}-acetyl-trifluoromethanesulphonamide

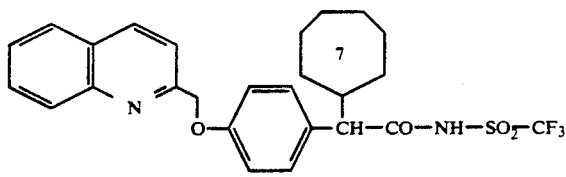

Analogously to the directions for Example 1 the title compound is prepared from 5.0 g (0.013 mol) of 1-[4-(quinolin-2-yl-methoxy)phenyl]-1-cycloheptyl-acetic acid, 2.5 g (0.02 mol) of dimethylaminopyridine, 2.0 g (0.013 mol) of trifluoromethanesulphonamide and 3.8 g (0.02 mol) of N-(3-dimethylaminopropyl)-N'-ethyl-carbodiimide hydrochloride. Yield: 5.0 g (75% of theory) of colourless crystals. M.p.: 210° C. (dec.).

EXAMPLE 15

N-{1-[4-(quinolin-2-yl-methoxy)phenyl]-1-cycloheptyl}-acetyl-o-tolylsulphonamide

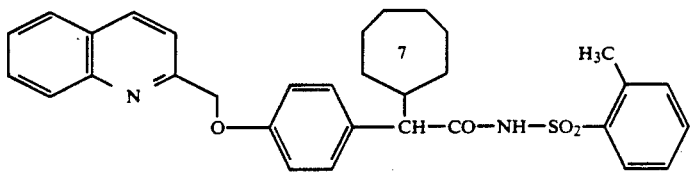

Analogously to the directions for Example 1 the title compound is prepared from 4 g (0.074 mol) of 1-[4-(quinolin-2-yl-methoxy)phenyl]-1-cycloheptyl-acetic acid, 0.9 g (0.0074 mol) of dimethylaminopyridine, 1.25 g (0.0074 mol) of o-tolylsulphonamide and 1.5 g (0.008 mol) of N-(3-dimethylaminopropyl)-N'-ethyl-carbodiimide hydrochloride. Yield: 2.4 g (60% of theory) of colourless crystals. M.p.: 83°-5° C. (dec.).

EXAMPLE 16

N-{1-[4-(quinolin-2-yl-methoxy)phenyl]-cyclooctyl}-acetyl-methanesulphonamide

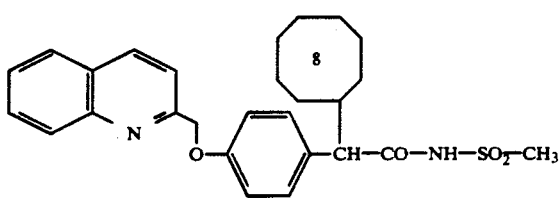

Analogously to the directions for Example 1 the title compound is prepared from 1.9 g (0.0047 mol) of 1-[4-(quinolin-2-yl-methoxy)phenyl]-1-cyclooctyl-acetic acid, 0.7 g (0.0047 mol) of dimethylaminopyridine, 0.5 g (0.0047 mol) of methanesulphonamide and 1.1 g (0.0057 mol) of N-(3-dimethylaminopropyl)-N'-ethyl-carbodiimide hydrochloride. Yield: 1.0 g (44% of theory) of colourless amorphous product. no M.p.

EXAMPLE 17

N-{1-[4-(quinolin-2-yl-methoxy)phenyl]-cyclodecyl}-acetyl-methanesulphonamide

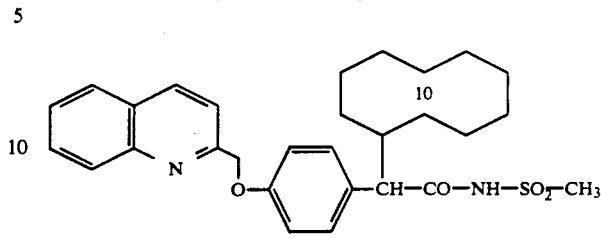

Analogously to the directions for Example 1 the title compound is prepared from 0.8 g (0.00185 mol) of 1-[4-(quinolin-2-yl-methoxy)phenyl]-1-cyclodecyl-acetic acid, 0.35 g (0.0026 mol) of dimethylaminopyridine, 0.2 g (0.0021 mol) of methanesulphonamide and 0.5 g (0.0026 mol) of N-(3-dimethylaminopropyl)-N'-ethyl-carbodiimide hydrochloride. Yield: 0.4 g (42.5% of theory) of colourless amorphous product. no M.p.

EXAMPLE 18

N-{1-[4-(quinolin-2-yl-methoxy)phenyl]-cyclodecyl}- acetyl-methanesulphonamide

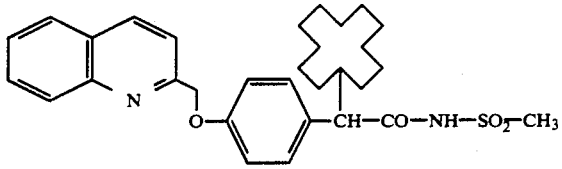

Analogously to the directions for Example 1 the title compound is prepared from 1.4 g (0.003 mol) of 1-[4-(quinolin-2-yl-methoxy)phenyl]-1-cyclododecyl-acetic acid, 0.5 g (0.0036 mol) of dimethylaminopyridine, 0.3 g (0.003 mol) of methanesulphonamide and 0.7 g (0.0036 mol) of N-3-dimethylaminopropyl)-N'-ethyl-carbodiimide hydrochloride. Yield: 0.9 g (56% of theory) of a colourless amorphous product. no M.p.

TITLE COMPOUNDS (FORMULA II)

EXAMPLE I

1-[4-(quinolin-2-yl-methoxy)phenyl]-1-cyclooctyl acetic acid

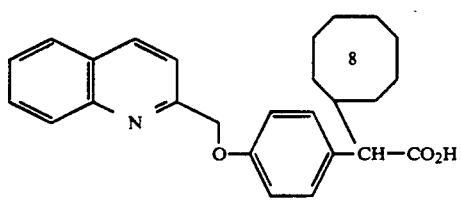

2.9 g (0.0069 mol) of 1-[4-(quinolin-2-yl-methoxy)-phenyl]-1-cyclooctyl acetic acid methylester were heated to boiling overnight in a mixture (50:50) of isopropanol and dioxane and 15 ml of 1 n sodium hydroxide solution. After cooling, 15 ml of 1 n hydrochloric acid were added and the precipitate obtained was filtered off. Yield: 2.8 g (quantitative) of colourless crystals. M.p. 157° C.

EXAMPLE II

1-[4-(quinolin-2-yl-methoxy)phenyl]-1-cyclooctyl acetic acid methyl ester

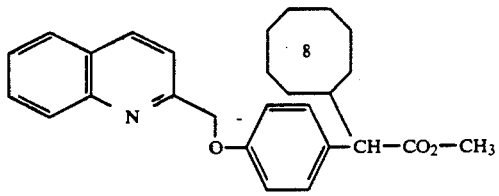

0.6 g (80% strength=0.02 mol) of sodium hydride was suspended in 20 ml of dried DMF under an argon atmosphere, 6.1 g (0.02 mol) of 4-(quinolin-2-yl-methoxy)phenyl acetic acid methyl ester in 50 ml of dried DMF were added and the mixture was heated slowly for 1 hour with stirring to 25° C., during which process gas evolved. Then 5.8 g (0.03 mol) of cyclooctyl bromide were added, whereupon the temperature rose to 35° C. Then the mixture was allowed to react further overnight, during the course of which the temperature fell to room temperature. 20 ml of 1 n hydrochloric acid were added, the mixture was evaporated to dryness and the residue was extracted by stirring with 50 ml of dichloromethane (gentle heating). The dichloromethane phase was extracted by shaking with 1 n NaHCO3 solution, dried with sodium sulphate, concentrated into a small volume and the residue was separated by column chromatography. Toluene/Ethyl acetate=9:1, silica gel:60. Yield: 2.8 g (25% of theory) of colourless crystals. M.p. 90° C.

EXAMPLE III

1-[4-(quinolin-2-yl-methoxy)phenyl]-1-cyclodecyl acetic acid

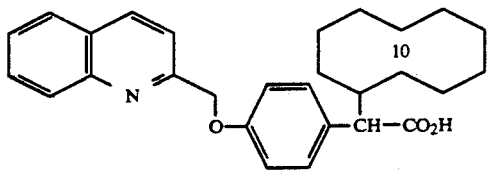

Analogously to the directions for Example I, the title compound is prepared from 1.9 g (0.0043 mol) of 1-[4-(quinolin-2-yl-methoxy)phenyl]-1-cyclodecyl-acetic acid methyl ester and 10 ml 1 n sodium hydroxide in 30 ml isopropanol. Yield: 1.6 g (86% of theory) of colourless crystals. M.p. 158° C.

EXAMPLE IV

1-[4-(quinolin-2-yl-methoxy)phenyl]-1-cyclodecyl acetic acid methyl ester

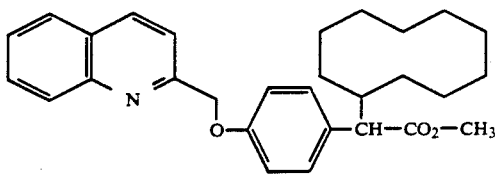

Analogously to the directions for Example II, the title compound is prepared from 6.1 g (0.02 mol) of 4-quinolin-2-yl-methoxy)phenylacetic methyl ester and 6.6 g (0.03 mol) cyclodecylbromide. Yield: 1.9 g (21% of theory) of a light yellow oil

EXAMPLE V

1-[4-(quinolin-2-yl-methoxy)phenyl]-1-cyclododecyl acetic acid

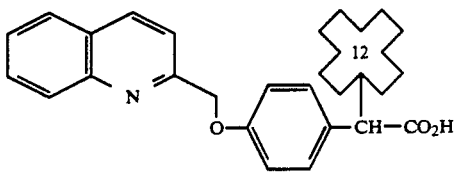

Analogously to the directions for Example I, the title compound is prepared from 2.4 g (0.00507 mol) 1-[4-quinolin-2-yl-methoxy)phenyl]-1-cyclododecyl-acetic acid methyl ester and 15 ml 1 n sodium hydroxide in 30 ml isopropanol. Yield: 2.3 g (quantitative) colourless crystals. M.p. 201° C.

EXAMPLE VI

1-[4-(quinolin-2-yl-methoxy)phenyl]-1-cyclododecyl acetic acid methyl ester

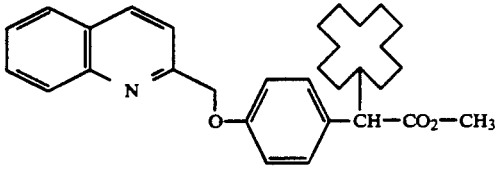

Analogously to the directions for Example II, the title compound is prepared from 6.1 g (0.002 mol) 4-(quinolin-2-yl-methoxy)phenyl-acetic acid methyl ester and 7.5 g (0.03 mol) cyclododecylbromide. Yield: 2.5 g (26% of theory) colourless crystals. M.p. 116° C.

EXAMPLE VII and VIII (+)-N-[1-[4-(Quinoline-2-yl-methoxy)phenyl-1-cycloheptyl]-acetyl-methanesulfonamide and (−)-N-[1-[4-Quinoline-2-yl-methoxy)phenyl-1-cycloheptyl]-acetyl-methanesulfonamide and

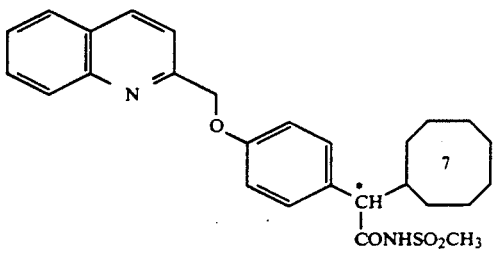

(+) resp.
(−) -Enantiomeres

Analogeously to the directions for example 1, the title compounds are prepared from the corresponding enantiomeric acetic acids.
(+)-enantiomer: M.p.: 172° C., $a_D = +14.24°$ C.
(−)-enantiomer: M.p.: 172° C., $a_D = -13,64°$ C.
(+)-[1-[4-(Quinoline-2-yl-methoxy)phenyl-1-cycloheptyl]-acetic acid
$a_D = +33,2°$ C., C=0.8 (acetone)
(−)-[1-[4-(Quinoline-2-yl-methoxy)phenyl-1-cycloheptyl]-acetic acid
$a_D = -32,2°$ C., C=0.7 (acetone)

It will be appreciated that the instant specification and claims are set forth by way of illustration and not limitation, and that various modifications and changes may be made without departing from the spirit and scope of the present invention.

What is claimed is:

1. A (quinolin-2-yl-methoxy)phenylacyl-sulphonamide or -cyanamide of the formula

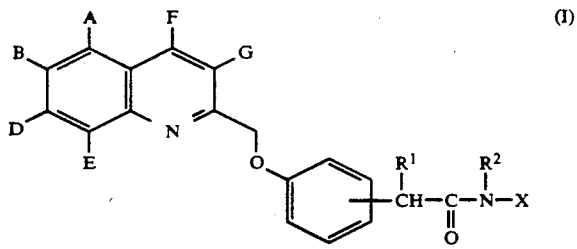

in which
A, B, D, E, F and G are identical or different and
represent hydrogen, hydroxyl, halogen, carboxyl, nitro, trifluoromethyl, trifluoromethoxy or a group of the formula —NR$^3$R$^4$, in which R$^3$ and R$^4$ are identical or different and denote hydrogen, straight-chain or branched alkyl having up to 8 carbon atoms or aryl having 6 to 10 carbon atoms,
represent straight-chain or branched alkyl, alkoxy or alkoxycarbonyl, in each case having up to 12 carbon atoms, and each of which is unsubstituted or substituted by hydroxyl, halogen, nitro, cyano or a group of the formula —NR$^3$R$^4$, in which R$^3$ and R$^4$ have the abovementioned meanings,
represent aryl having 6 to 10 carbon atoms, which is unsubstituted or substituted by halogen, hydroxyl, nitro, cyano, straight-chain or branched alkyl, alkoxy or alkoxycarbonyl in each case having up to 8 carbon atoms or by a group of the formula —NR$^3$R$^4$, in which R$^3$ and R$^4$ have the abovementioned meanings, R$^1$ represents cycloalkyl having 3 to 8 carbon atoms, which is unsubstituted or substituted by straight-chain or branched alkyl having up to 8 carbon atoms, R$^2$ represents hydrogen or
straight-chain or branched alkyl having up to 10 carbon atoms, which is unsubstituted or substituted by hydroxyl, alkoxy having up to 8 carbon atoms, halogen or by cycloalkyl having 3 to 8 carbon atoms or aryl having 6 to 10 carbon atoms, which in turn is unsubstituted or substituted by straight-chain or branched alkyl having up to 8 carbon atoms, halogen, nitro, hydroxyl or cyano, or
represents cycloalkyl having 3 to 8 carbon atoms which is unsubstituted or substituted by straight-chain or branched alkyl having up to 8 carbon atoms, or
represents an alkali metal, X represents a group of the formula —SO$_2$—R$^5$, in which
R$^5$ is trifluoromethyl or straight-chain or branched alkyl having up to 10 carbon atoms, which is unsubstituted or substituted by hydroxyl, halogen, cyano, alkoxy or alkoxycarbonyl in each case having up to 8 carbon atoms or by aryl having 6 to 10 carbon atoms, which is unsubstituted or substituted by halogen, nitro, cyano or straight-chain or branched alkyl or alkoxy in each case having up to 8 carbon atoms, or
is aryl having 6 to 10 carbon atoms, which is unsubstituted or substituted by halogen, nitro, cyano, hydroxyl, straight-chain or branched alkyl, alkoxy or alkoxycarbonyl in each case having up to 8 carbon atoms, trifluoromethyl or trifluoromethoxy, or X represents cyano or a physiologically acceptable salt thereof.

2. A (quinolin-2-yl-methoxy)phenylacyl-sulphonamide or -cyanamide of the formula (I) according to claim 1 in which
A, B, D, E, F and G are identical different and
represent hydrogen, hydroxyl, fluorine, chlorine, bromine, carboxyl, nitro, trifluoromethyl, trifluoromethoxy or a group of the formula —NR$^3$R$^4$, in which R$^3$ and R$^4$ are identical or different and denote hydrogen, straight-chain or branched alkyl having up to 6 carbon atoms or phenyl,
represent straight-chain or branched alkyl, alkoxy or alkoxycarbonyl in each case having up to 10 carbon atoms, and each of which is unsubstituted or substituted by hydroxyl, fluorine, chlorine, bromine, nitro, cyano or a group of the formula —NR$^3$R$^4$, in which R$^3$ and R$^4$ have the abovementioned meanings,
represent phenyl which is unsubstituted or substituted by fluorine, chlorine, bromine, hydroxyl, nitro, cyano, straight-chain or branched alkyl, alkoxy or alkoxycarbonyl in each case having up to 6 carbon atoms or by a group of the formula —NR³R⁴, in which R³ and R⁴ have the above-mentioned meanings, R¹ represents cyclopropyl, cyclobutyl, cyclopentyl, cyclohexyl or cycloheptyl, each of which is unsubstituted or substituted by straight-chain or branched alkyl having up to 6 carbon atoms, R² represents hydrogen or
straight-chain or branched alkyl having up to 8 carbon atoms, which is unsubstituted or substituted by hydroxyl, alkoxy having up to 6 carbon atoms, fluorine, chlorine, bromine, cyclopropyl, cyclobutyl, cyclopentyl, cyclohexyl, cycloheptyl or phenyl, which in turn is unsubstituted or substituted by straight-chain or branched alkyl having up to 6 carbon atoms, fluorine, chlorine or bromine, or
represents cyclopropyl, cyclohexyl, cyclopentyl, cyclohexyl or cycloheptyl, each of which is unsubstituted or substituted by straight-chain or branched alkyl having up to 6 carbon atoms, or
represents sodium or potassium, X represents a group of the formula —SO₂—R⁵, in which
R⁵ is trifluoromethyl or straight-chain or branched alkyl having up to 8 carbon atoms, which is unsubstituted or substituted by fluorine, chlorine, bromine, alkoxycarbonyl in each case having up to 6 carbon atoms or by phenyl, which in turn is unsubstituted or substituted by fluorine, chlorine, bromine or by straight-chain or branched alkyl or alkoxy in each case having up to 6 carbon atoms, or
is phenyl which is unsubstituted or substituted by fluorine, chlorine, bromine, nitro, cyano, straight-chain or branched alkyl, alkoxy or alkoxycarbonyl in each case having up to 6 carbon atoms or trifluoromethyl, or X represents cyano
or a physiologically acceptable salt thereof.

3. A (quinolin-2-yl-methoxy)phenylacyl-sulphonamide or -cyanamide of the formula (I) according to claim 1 in which
A, B, D, E, F and G are identical or different and represent hydrogen, fluorine, chlorine, bromine, nitro or trifluoromethyl,
represent methyl, ethyl, propyl, isopropyl, butyl or tert.butyl, R¹ represents cyclopropyl, cyclobutyl, cyclopentyl, cyclohexyl or cycloheptyl, each of which is unsubstituted or substituted by methyl, ethyl, propyl or isopropyl, R² represents hydrogen or
straight-chain or branched alkyl having up to 6 carbon atoms, which is unsubstituted or substituted by cyclopropyl, cyclopentyl, cyclohexyl or cycloheptyl,
represents cyclopropyl, cyclopentyl, cyclohexyl or cycloheptyl, or
represents sodium, X represents a group of the formula —SO₂—R⁵, in which
R⁵ is trifluoromethyl, straight-chain or branched alkyl having up to 6 carbon atoms, which is unsubstituted or substituted by phenyl which in turn is substituted by fluorine, chlorine or by straight-chain or branched alkyl having up to 4 carbon atoms, or
is phenyl which is unsubstituted or substituted by fluorine, chlorine or straight-chain or branched alkyl having up to 4 carbon atoms, or X represents cyano
or a physiologically acceptable salt thereof.

4. N-{1-[4-(Quinolin-2-yl-methoxy)phenyl]-1-cyclopentyl}-acetyl-o-tolylsulphonamide of the formula

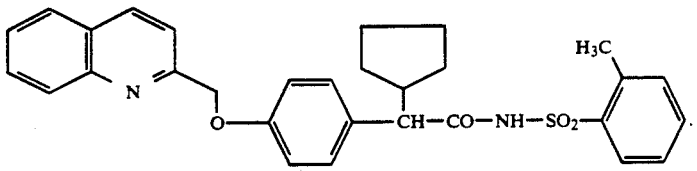

5. N-{1-[4-(Quinolin-2-yl-methoxy)phenyl]-1-cyclopentyl}-acetyl-trifluoromethanesulphonamide of the formula

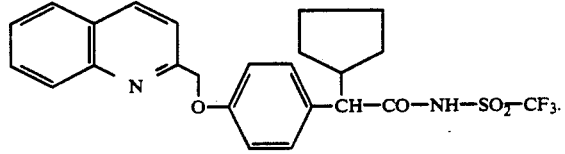

6. N-Methyl-N-{1-[4-(quinolin-2-yl-methoxy)-phenyl]-1-cyclopentyl-acetyl-}-trifluoromethanesulphonamide of the formula

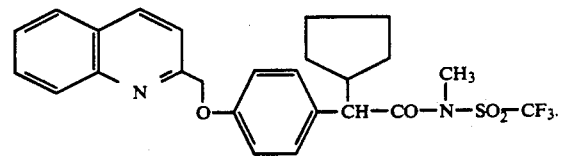

7. N-{1-[4-(Quinolin-2-yl-methoxy)phenyl]-1-cyclopentyl}-acetyl-cyanamide of the formula

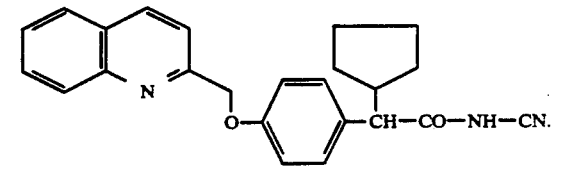

8. A composition for inhibiting enzymatic reactions in the context of arachidonic acid metabolism consisting essentially of an enzymatic inhibitory effective amount of a (quinolin-2-yl-methoxy)phenylacyl-sulphonamide or -cyanamide according to claim 1 in admixture with a pharmaceutically acceptable carrier.

9. A unit dose of a composition according to claim 8 in the form of a tablet, capsule or ampoule.

10. A method of inhibiting enzymatic reactions in the context of arachidonic acid metabolism in a patient consisting essentially of administering to said patient an enzymatic inhibitory effective amount of a (quinolin-2-yl-methoxy)phenylacyl-sulphonamide or -cyanamide according to claim 1, either alone or in admixture with a physiologically acceptable diluent.

11. A method according to claim 10, wherein the (quinolin-2-yl-methoxy)phenylacyl-sulphonamide or -cyanamide is selected from the group consisting of
N-{1-[4-quinolin-2-yl-methoxy)phenyl]-1-cyclopentyl}-acetyl-o-tolylsulphonamide,
N-{1-[4-(quinolin-2-yl-methoxy)phenyl]-1-cyclopentyl}-acetyl-trifluoromethanesulphonamide,
N-methyl-N-{1-[4-(quinolin-2-yl-methoxy)phenyl]-1-cyclopentyl-acetyl}-trifluoromethanesulphonamide, and
N-{1-[4-quinolin-2-yl-methoxy)phenyl]-1-cyclopentyl}-acetyl-cyanamide.

12. A method according to claim 11, wherein the enzymatic reaction in the context of arachidonic acid metabolism is lipoxygenase.

13. A method of treating a patient suffering from allergies, bronchitis, emphysema, shock lung, pulmonary hypertension, inflammation, oedemas, thromboses, thromboemolisms, ischaemias, cardiac infarct, cerebral infarct, cardiac arrhythmia, angina pectoris, arteriosclerosis or dermatoses comprising administering to said patient an effective amount of a (quinolin-2-yl-methoxy)-phenylacyl-sulphonamide or -cyanamide according to claim 1, either alone or in admixture with a physiologically acceptable diluent.

14. A method according to claim 13, wherein the (quinolin-2-yl-methoxy)phenylacyl-sulphonamide or -cyanamide is selected from the group consisting of
N-{1-[4-(quinolin-2-yl-methoxy)phenyl]-1-cyclopentyl}-acetyl-o-tolylsulphonamide,
N-{1-[4-(quinolin-2-yl-methoxy)phenyl]-1-cyclopentyl}-acetyl-trifluoromethanesulphonamide,
N-methyl-N-{1-[4-(quinolin-2-yl-methoxy)phenyl]-1-cyclopentyl-acetyl}-trifluoromethanesulphonamide, and
N-{1-[4-(quinolin-2-yl-methoxy)phenyl]-1-cyclopentyl}-acetyl-cyanamide.

15. (+)-Enantiomeres and (−)-Enantiomeres of substituted (quinoline-2-yl-methoxy)phenyl-acyl-sulfonamides and -cyanamides according to claim 1.

16. (+)-N-[1-[4-(Quinoline-2-yl-methoxy)phenyl-1-cycloheptyl]-acetyl-methanesulfonamide.

17. (−)-N-[1-[4-Quinoline-2-yl-methoxy)phenyl-1-cycloheptyl]-acetyl-methanesulfonamide.

* * * * *

UNITED STATES PATENT AND TRADEMARK OFFICE
CERTIFICATE OF CORRECTION

PATENT NO. : 5,091,392

DATED : February 25, 1992

INVENTOR(S) : Raddatz et al.

It is certified that error appears in the above-identified patent and that said Letters Patent is hereby corrected as shown below:

Title Page      ABSTRACT: Line 8 delete " $-NH^3R^4$ " and substitute -- $-NR^3R^4$ --

Col. 24, claim 2     After " identical " insert -- or --

Signed and Sealed this

Second Day of November, 1993

Attest:

BRUCE LEHMAN

*Attesting Officer*     *Commissioner of Patents and Trademarks*